US007625726B2

(12) United States Patent
Gu et al.

(10) Patent No.: US 7,625,726 B2
(45) Date of Patent: Dec. 1, 2009

(54) PROCESS FOR PREPARING RAPAMYCIN 42-ESTERS AND FK-506 32-ESTERS WITH DICARBOXYLIC ACID, PRECURSORS FOR RAPAMYCIN CONJUGATES AND ANTIBODIES

(75) Inventors: Jianxin Gu, River Edge, NJ (US); Ping Cai, New City, NY (US); Mark E. Ruppen, Garnerville, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 12/240,230

(22) Filed: Sep. 29, 2008

(65) Prior Publication Data

US 2009/0029426 A1 Jan. 29, 2009

Related U.S. Application Data

(62) Division of application No. 11/104,349, filed on Apr. 12, 2005, now Pat. No. 7,445,916.

(60) Provisional application No. 60/561,966, filed on Apr. 14, 2004.

(51) Int. Cl.
*C12P 17/16* (2006.01)
*C12P 17/18* (2006.01)

(52) U.S. Cl. ...................... 435/118; 435/119

(58) Field of Classification Search ........................ None
See application file for complete search history.

(56) References Cited

U.S. PATENT DOCUMENTS

| 3,929,992 A | 12/1975 | Sehgal et al. |
| 5,023,264 A | 6/1991 | Caufield et al. |
| 5,078,999 A | 1/1992 | Warner et al. |
| 5,080,899 A | 1/1992 | Sturm et al. |
| 5,100,883 A | 3/1992 | Schiehser et al. |
| 5,118,667 A | 6/1992 | Adams et al. |
| 5,120,842 A | 6/1992 | Failli et al. |
| 5,130,307 A | 7/1992 | Failli et al. |
| 5,162,333 A | 11/1992 | Failli et al. |
| 5,177,203 A | 1/1993 | Failli et al. |
| 5,221,670 A | 6/1993 | Caufield |
| 5,233,036 A | 8/1993 | Hughes |
| 5,256,790 A | 10/1993 | Nelson |
| 5,258,389 A | 11/1993 | Gooulet et al. |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson |
| 5,385,909 A | 1/1995 | Nelson |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,463,048 A | 10/1995 | Skotnicki et al. |
| 5,480,988 A | 1/1996 | Kao et al. |
| 5,480,989 A | 1/1996 | Kao et al. |
| 5,489,680 A | 2/1996 | Failli et al. |
| 5,491,231 A | 2/1996 | Nelson |
| 5,504,091 A | 4/1996 | Molnar-Komber et al. |
| 5,563,145 A | 10/1996 | Failli et al. |
| 5,665,772 A | 9/1997 | Cottens et al. |
| 5,780,462 A | 7/1998 | Lee et al. |
| 6,261,813 B1 | 7/2001 | Khmelnitsky |
| 6,277,983 B1 | 8/2001 | Shaw et al. |
| 6,745,478 B2 | 6/2004 | DeLillo |
| 7,153,957 B2 | 12/2006 | Chew et al. |
| 7,202,256 B2 | 4/2007 | Gu et al. |
| 7,268,144 B2 | 9/2007 | Gu et al. |
| 7,445,916 B2 * | 11/2008 | Gu et al. ..................... 435/118 |
| 2005/0234087 A1 | 10/2005 | Gu et al. |
| 2006/0069161 A1 * | 3/2006 | Lee et al. ..................... 514/570 |

FOREIGN PATENT DOCUMENTS

| EP | 0464 895 | 1/1992 |
| EP | 525960 | 3/1993 |
| GB | 2 281 294 | 3/1995 |
| WO | WO 92/05179 | 2/1992 |
| WO | WO 94/24304 | 10/1994 |
| WO | WO 94/25022 | 11/1994 |
| WO | WO 94/25072 | 11/1994 |
| WO | WO 95/28406 | 10/1995 |
| WO | WO 98/45333 | 10/1998 |

OTHER PUBLICATIONS

Gregory, "The use of new Antiproliferative Immunosuppressants is a Novel and Highly Affective Strategy for the Prevention of Vascular Occlusive Disease", J. Heart Lung Transplant, 11(1)(pt. 2):197 (Abstracts) (Jan.-Feb. 1992).
Adamczyk, "Lipase Mediated Hydrolysis of Rapamycin 42-Hemisuccinate Benzyl and Methyl Esters", Tetrahedron Letters, 35(7):1019-1022 (Feb. 14, 1994).
Khmelnitsky, "Synthesis of Water-Soluble Paclitaxel Derivatives by Enzymatic Acylation", J Am Chem Soc, 119(47):11554-11555 (Nov. 14, 1997).
Shibatani, "Enzymatic Synthesis of Vinyl Sugar Ester in Dimethylformamide, Biotechnology", Letters, 19(6):511-514 (Jun. 1997).
Park, "Enzyme-Catalyzed Synthesis of Sugar-Containing Monomers and Linear Polymers", Biotechnology and Bioengineering, 70(2):208-216 (Oct. 20, 2000).

* cited by examiner

*Primary Examiner*—Herbert J. Lilling
(74) *Attorney, Agent, or Firm*—David A. Rubin; Howson & Howson LLP

(57) ABSTRACT

Methods for the synthesis of regiospecific rapamycin 42-hemiesters and regiospecific FK506 32-esters with dicarboxylic acids is described. The methods involve catalyzing the reaction between a rapamycin or a FK-506 and a dicarboxylic anhydride or a bifunctional activated ester of dicarboxylic acid with a lipase.

25 Claims, No Drawings

PROCESS FOR PREPARING RAPAMYCIN 42-ESTERS AND FK-506 32-ESTERS WITH DICARBOXYLIC ACID, PRECURSORS FOR RAPAMYCIN CONJUGATES AND ANTIBODIES

CROSS-REFERENCE TO RELATED APPLICATIONS

This application is a divisional of U.S. patent application Ser. No. 11/404,349, filed Apr. 12, 2005, now U.S. Patent No. 7,445,916 issued Nov. 04, 2008,which claims the benefit of the priority of U.S. Provisional Patent Application No. 60/561,966, filed Apr. 14, 2004, now abandoned.

BACKGROUND OF THE INVENTION

Rapamycin is a macrocyclic triene antibiotic produced by *Streptomyces hygroscopicus* that was found to have antifungal activity, particularly against *Candida albicans*, both in vitro and in vivo. Rapamycin is available commercially as Rapamune® (Wyeth). Rapamycin has also been shown to be useful in antitumor compositions, as an immunosuppressive agent, in the treatment of rheumatoid arthritis; in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], adult T-cell leukemia/lymphoma [European Patent Application 525,960 A1, and smooth muscle cell proliferation and intimal thickening following vascular injury [R. Morris, *J. Heart Lung Transplant* 11 (pt. 2): 197 (1992)].

Rapamycin and its preparation are described in U.S. Pat. No. 3,929,992, issued Dec. 30, 1975. Rapamycin 42-ester with 3-hydroxy-2-(hydroxymethyl)-2-methylpropionic acid (CCI-779) is an ester of rapamycin which has demonstrated significant inhibitory effects on tumor growth in both in vitro and in vivo models. The preparation and use of hydroxyesters of rapamycin, including CCI-779, are disclosed in U.S. Pat. Nos. 5,362,718 and 6,277,983, and US Patent Publication No. US 2005-0033046 A1 (U.S. patent application Ser. No. 10/903,062).

Rapamycin derivatives at the 42-OH position have been synthesized and found to be useful for inducing immunosuppression, in the treatment of transplantation rejection, autoimmune diseases, solid tumors, adult T-cell leukemia/lymphoma, and hyperproliferative vascular disorders, among others. Some derivatives serve as the precursors for the synthesis of rapamycin conjugates of general formula (I) below, which are useful as immunogenic molecules for the generation of antibodies specific for rapamycin as well as for isolating rapamycin binding proteins for immunoassays, and for detecting antibodies specific for rapamycin or its derivatives thereof.

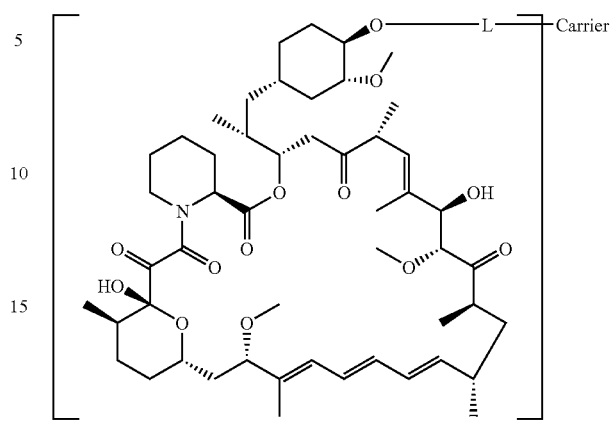

In formula I, the carrier is an immunogenic carrier material or detector carrier material such as a protein or polypeptide and L is a linker, which enables the rapamycin to be attached to the carrier. [US Patent Publication No. US 2004-0010920].

A number of 42-derivatives of rapamycin that can be used as linking groups for the preparation of conjugates have been described. For example, the preparation of fluorinated ester of rapamycin is described in U.S. Pat. No. 5,100,883, the preparation of amide esters is described in U.S. Pat. No. 5,118,667, the preparation of aminoesters is described in U.S. Pat. No. 5,130,307, the preparation of carbamates of rapamycin is described in U.S. Pat. No. 5,118,678, the preparation of sulfonates and sulfamates are described in U.S. Pat. No. 5,177,203, the preparation of 42-ester with succinic acid and other dicarboxylic acids (adipic acid, glutaric acid, diglycolic acid, etc) are described in US Patent Publication No. US 2001-0010920, U.S. Pat. No. 5,378,696, and International Patent Publication Nos. WO 98/45333, WO 94/25072, WO 94/25022, and WO 92/05179. In one embodiment, 42-esters with dicarboxylic acids, such as 42-hemisuccinate, 42-hemiglutarate and 42-hemiadipates (formula II) are used for the synthesis of rapamycin conjugate of formula I.

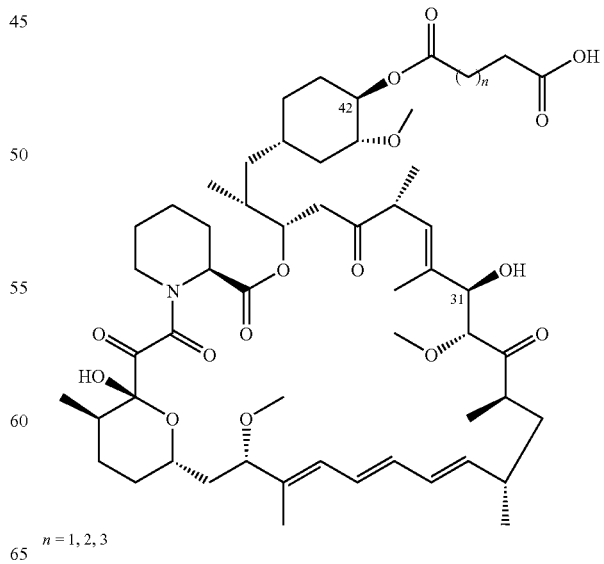

$n = 1, 2, 3$

The synthesis of a compound of formula (II) has been described as being carried out by direct esterification of 42-OH with a corresponding anhydride in the presence of a weak base. Due to the sensitivity of rapamycin to basic conditions, and along with the poor regioselectivity, the desired 42-hemiester is produced with poor yield (typically below 20%) after HPLC purification; the crude product is contaminated by 31,42-diester, 31-ester and other by-products

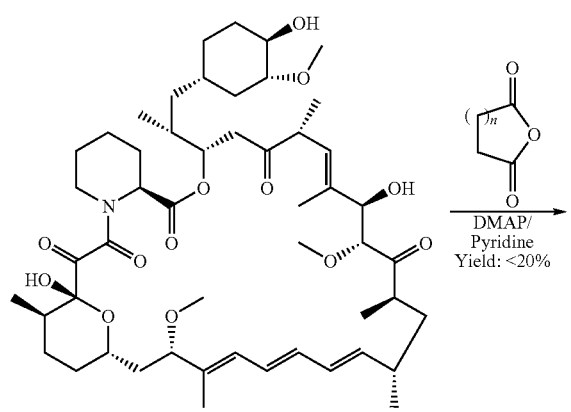

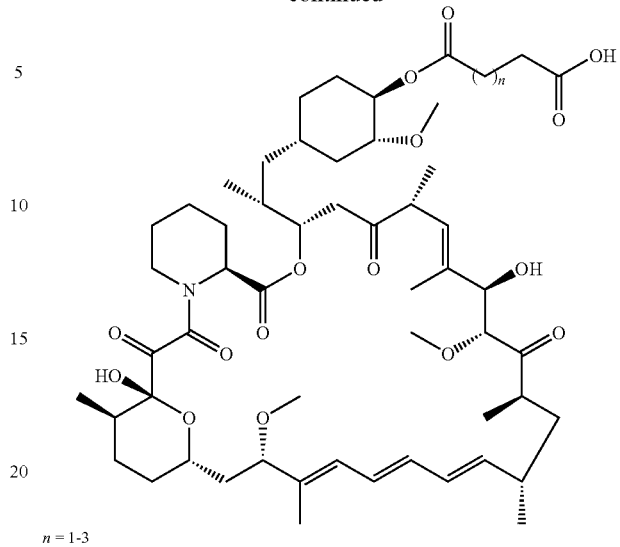

$n = 1-3$

In an effort to improve the yield for this process, a two-step lipase-catalyzed hydrolysis approach was used [M. Adamczyk, et al, *Tetrahedron Letters,* 35(7):1019-1022 (1994)], in which the corresponding benzyl and methyl ester of rapamycin of 42-hemisuccinate were hydrolyzed using lipase from *Pseudomonas* sp. A slightly improved yield was obtained (29% from benzyl ester and 50% from the methyl ester). However, the synthesis of rapamycin 42-hemisuccinate benzyl and methyl ester via conventional chemistry also suffers from poor regioselectivity, low yield and tedious purification steps.

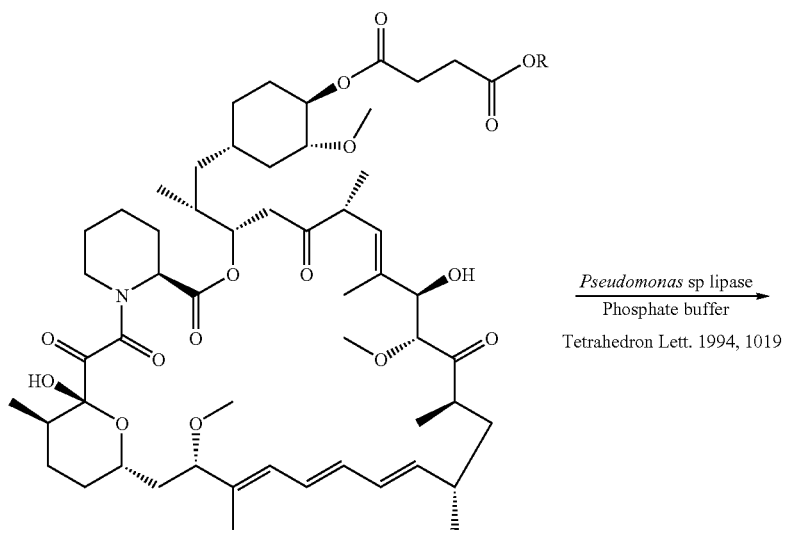

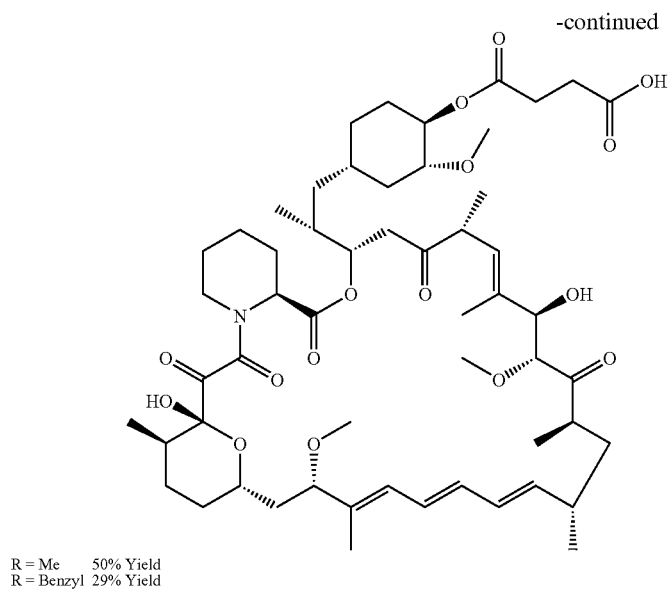

R = Me 50% Yield
R = Benzyl 29% Yield

There is therefore a need for an efficient synthesis of hemiesters with improved yield.

SUMMARY OF THE INVENTION

The present invention describes a process for the synthesis of rapamycin 42-hemiester of formula (II) from a rapamycin in the presence of a lipase, a hydrolytic enzyme. In another aspect, the process of the invention provides regiospecific production of FK-506 32-hemiester from an FK-506 in the presence of a lipase. The method of the invention provides a regioselective approach towards the synthesis of these compounds with excellent yield.

The present invention further provides methods of using the intermediate compounds produced according to the present invention for generating antibodies and conjugates.

DETAILED DESCRIPTION OF THE INVENTION

The method of the invention produces a rapamycin 42-hemiester (II) or a FK-506 hemiester which is a precursor for the preparation of a rapamycin conjugate.

As used herein, "a rapamycin" defines a class of immunosuppressive compounds which contain the basic rapamycin nucleus (shown below).

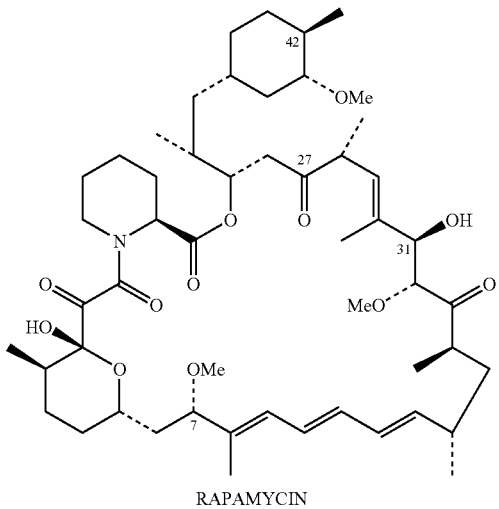

RAPAMYCIN

A rapamycin according to this invention includes compounds which may be chemically or biologically modified as derivatives of the rapamycin nucleus, while still retaining immunosuppressive properties. Accordingly, the term "a rapamycin" includes esters, ethers, oximes, hydrazones, and hydroxylamines of rapamycin, as well as rapamycins in which functional groups on the nucleus have been modified, for example through reduction or oxidation, a metabolite of rapamycin, or a ring opened rapamycin (such as secorapamycin, described in U.S. Pat. No. 5,252,579). The term "a rapamycin" also includes pharmaceutically acceptable salts of rapamycins, which are capable of forming such salts, either by virtue of containing an acidic or basic moiety.

However, such compounds retain the hydroxyl groups at the 42-position in order to permit the production of regiospecific 42-hemiesters of the invention.

In one embodiment, the esters and ethers of rapamycin useful in the invention are of the hydroxyl groups at the 31-position of the rapamycin nucleus, esters and ethers of a hydroxyl group at the 27-position (following chemical reduction of the 27-ketone), and that the oximes, hydrazones, and hydroxylamines are of a ketone of the rapamycin nucleus.

In other embodiments, 31-esters and ethers of rapamycin useful in the invention are described in the following patents: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat.

No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers is described in the patents listed above.

In still other embodiments, 27-esters and ethers of rapamycin useful in the invention are disclosed in U.S. Pat. No. 5,256,790. The preparation of these esters and ethers is described in the patents listed above.

In other embodiments, oximes, hydrazones, and hydroxylamines of rapamycin useful in the invention are disclosed in U.S. Pat. Nos. 5,373,014, 5,378,836, 5,023,264, and 5,563, 145. The preparation of these oximes, hydrazones, and hydroxylamines are disclosed in the above-listed patents.

In additional embodiments, rapamycins useful in the invention include rapamycin [U.S. Pat. No. 3,929,992], proline-rapamycin, 7-desmethyl rapamycin, 32-desmethyl rapamycin, 32-desmethoxy rapamycin and their derivatives as described above.

In still other embodiments, the method of the invention can be used to prepare 32-esters of FK-506 (formula III) from an PK-506 compound having the structure illustrated below.

III

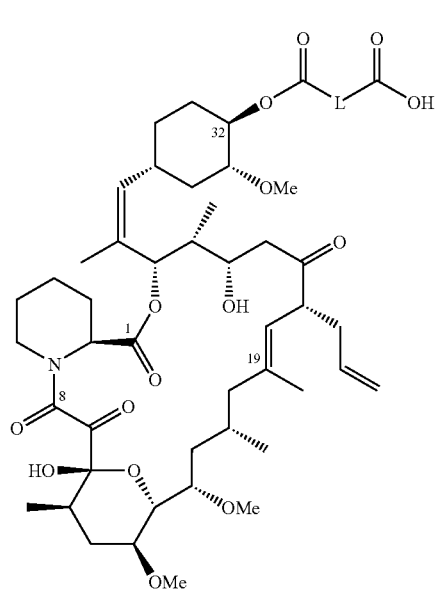

In one embodiment, the preparation of formula (II) or FK-506 32-ester (formula III) via lipase-catalyzed esterification is carried out by using corresponding carboxylic anhydrides as acylating agents. This one-step method provides a robust process for formula (II) or formula (III). In another aspect, the preparation of a hemiester of the invention is carried out using bifunctional activated ester of corresponding di-carboxylic acids including di(vinyl), di(isopropenyl), di(N-succinimidyl) esters of dicarboxylic acids as acylating donor in the presence of a lipase. The resulting ester intermediate is then hydrolyzed with water catalyzed by another lipase to furnish the hemiester.

I. Using Dicarboxylic Anhydrides as Acylating Agents

The following scheme illustrates the preparation of rapamycin 42-hemiesters (II) from rapamycin and dicarboxylic anhydrides in the presence of a lipase in a suitable solvent.

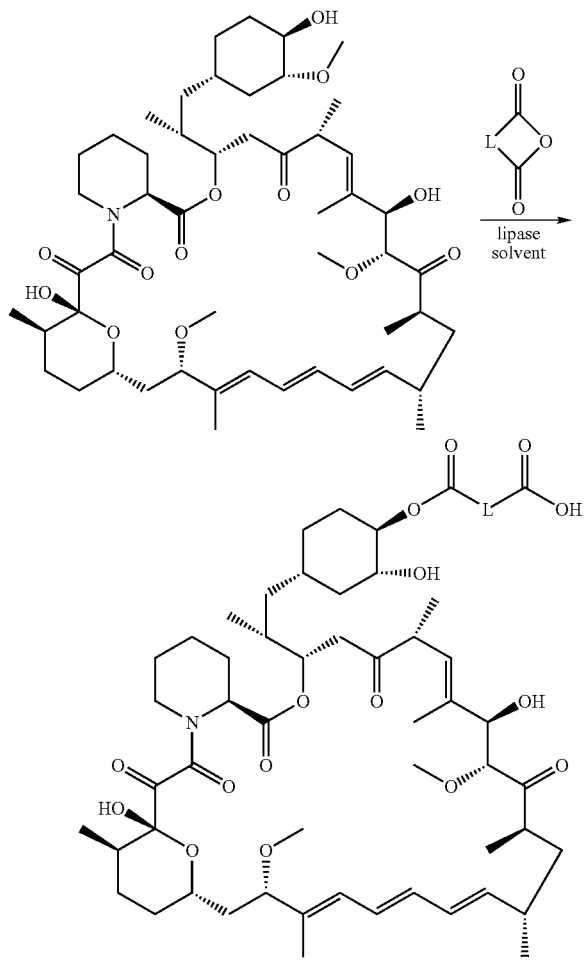

Similarly, a FK-506 32-hemiester can be prepared from an FK-506 and dicarboxylic anhydrides using a FK-506 as the starting material.

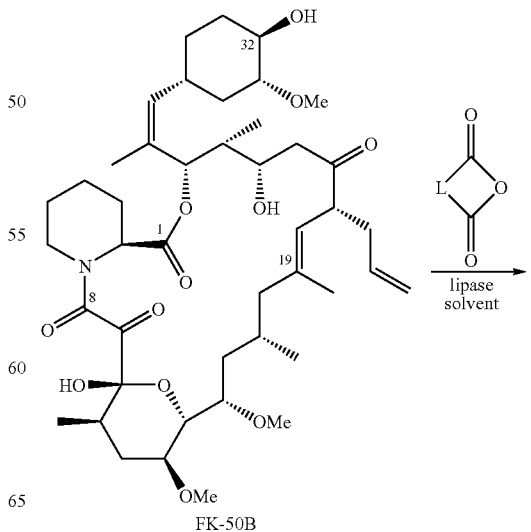

FK-50B

-continued

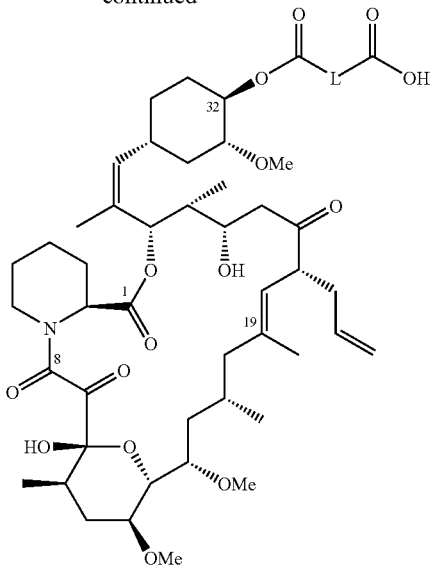

For convenience, the following discussion will refer to a rapamycin and rapamycin 42-esters. However, it should be understood that FK-506 and FK-506 32-ester can be readily substituted throughout the specification for a rapamycin and a rapamycin 42-hemiester.

With reference to the above schemes, L is a linking group. In this embodiment, suitable linking groups are readily selected from a straight chain or branched chain, having 1 to 6 carbon atoms or 2 to 4 carbon atoms. Examples of suitable linking groups, L, include, without limitation, linear or branched alkylenes, such as, dimethylene, trimethylene, tetramethylene, and 2-methyl-trimethylene. Still other suitable linking groups will be readily apparent to one of skill in the art.

In the above schemes, the dicarboxylic anhydride is illustrated by the following structure

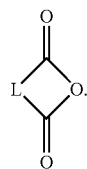

One of skill in the art can readily select appropriate dicarboxylic anhydride, given the definition of the linking group above. Examples of suitable dicarboxylic anhydrides include succinic anhydride, glutaric anhydride, 3-methylglutaric anhydride, and mixtures thereof.

In one embodiment, lipases useful in the present invention are chosen from lipases with microbial origin, termed "microbial lipases". Microbial lipases include, for example, *Candida antarctica, Candida rugosa, Mucor miehei, Pseudomonas cepacia, Pseudomonas fluorescens, Rhizopus delemar*, and *Aspergillus niger*. In another embodiment, the lipase from *Candida antarctica*, type B is used in the practice of this invention. *C. antarctica* lipase is commercially available, e.g., under the product designation NOVO SP435 or NOVOZYM 435 from Novo Nordisk, or CHIRAZYME L-2 from Roche Molecular Biochemicals and BioCatalytics. In yet another embodiment, the lipase is lipase PS-C "Amano" II from Amano Enzyme, described herein. Lipases useful in the present invention can be used in crude, partially purified, purified or immobilized form from different microbial origin, and under different trade names by various suppliers.

The lipase is used in an effective catalytic amount, i.e., an amount which effectively catalyzes the acylation reaction at a reasonable rate. Those skilled in the art will appreciate that the enzyme can be used in amounts of about 100 to about 800 wt % (relative to the amount of rapamycin). In one embodiment, the enzyme is used in amounts of about 200 to about 700 wt %, about 250 to about 600 wt %, or about 300 to about 500 wt %.

The reactions of the invention are typically carried out in a suitable solvent. The solvent is used in an amount which can effectively dissolve all or part of the starting rapamycin [or FK-506] at the beginning and allows the reaction to proceed at a reasonable rate. Representative examples of solvent useful in the present invention include toluene, tert-butyl methyl ether (TBME), tetrahydrofuran (THF), acetonitrile (MeCN), 1,4-dioxane, $CH_2Cl_2$, $CHCl_3$, ethyl ether, hexane, acetonitrile ($CH_3CN$), dimethylsulfone (DMSO) and mixtures thereof. In one embodiment, a mixture of toluene-$CH_3CN$ is used. In a further embodiment, toluene-$CH_3CN$ is present in a ratio of about 1:1 to about 10:1 (v/v), or about 3:1 to 7:1 (v/v). In yet another embodiment, toluene is used as solvent. In still another embodiment, toluene-$CH_3CN$ (5:1 v/v) is used.

The reactions of the invention are conducted at a temperature low enough to reduce the formation of unwanted by-product, but not so low as to require an unreasonably long reaction time. A suitable temperature for this enzymatic process can be in the range of about 20° C. to about 75° C., about 25 to 27° C. to 75° C., about 30° C. to 40° C. to about 700° C., about 32° C. to 37° C. to about 65° C. In one embodiment, the temperature is about 30° C. to about 650° C., or about 400° C. to 55° C.

In one embodiment, the method of the invention is conducted in accordance with the following procedure. A rapamycin [or FK-506], an anhydride and a lipase are admixed in a solvent. The mixture is then heated at 40° C. to 60° C. under argon (Ar) or nitrogen ($N_2$) atmosphere for 1 to 7 days. The enzyme is then separated from the reaction mixture via filtration. The product is then purified via recrystallization or silica gel column chromatography.

The reaction can be monitored by various techniques such as thin layer chromatography (TLC) and high performance liquid chromatography (HPLC). Alternatively, other monitoring methods can be used by one of skill in the art. When the reaction is completed, the enzyme (lipase) is filtered off and washed with a suitable solvent. The solvent may be the same as selected for use in the reaction, or may differ from the solvent in the reaction. Where the solvent differs, it can be chosen from among the solvents defined above, or other commonly-used solvents, such as acetone, ethyl acetate, methanol, ethanol, isopropanol, among others. The solvent can then be evaporated off under suitable conditions, e.g., reduced pressure.

In one embodiment, the solvent is selected to minimize water content in the reaction. Additionally, or alternatively, a molecular sieve can be applied to the reaction and/or drying agents can be added to the reaction. However, limitation of the water content of the reaction is not critical to this aspect of the invention.

The residue is then purified by suitable means, e.g., by silica gel column chromatography, elution with a suitable solvent, or recrystallization with a suitable solvent (e.g., hexane-acetone, hexane-ethyl acetate, ethyl ether, among others). Other purification means are known to those of skill in the art and are contemplated by the invention.

In one embodiment, if the reaction does not finish after certain period time as stated above, additional enzyme can be added, and the mixture stirred for a further period of time until the reaction was completed as judged by TLC or HPLC.

Example 1 below illustrates this one-step, highly regioselective process through the synthesis of rapamycin 42-hemisuccinate.

II. Using Bifunctional Activated Dicarboxylic Esters as Acylating Agents

The following scheme illustrates the preparation of a rapamycin 42-hemiester (II) from a rapamycin and a bifunctional dicarboxylic ester. Also, an FK-506 hemiester can be prepared from an FK-506 and a bifunctional dicarboxylic ester using these methods. It will be readily understood that where the following specification refers to rapamycin, FK-506 can be substituted in order to produce an FK-506 32-ester.

The method of the invention involves two steps. The first step is performed by mixing rapamycin (or FK-506) and a bifunctional dicarboxylic ester with a lipase of microbial origin as defined above, in a suitable solvent, as defined above. The second step is hydrolysis of resulting ester intermediate using lipase to furnish the desired compound of formula (II) (or FK-506 32-ester).

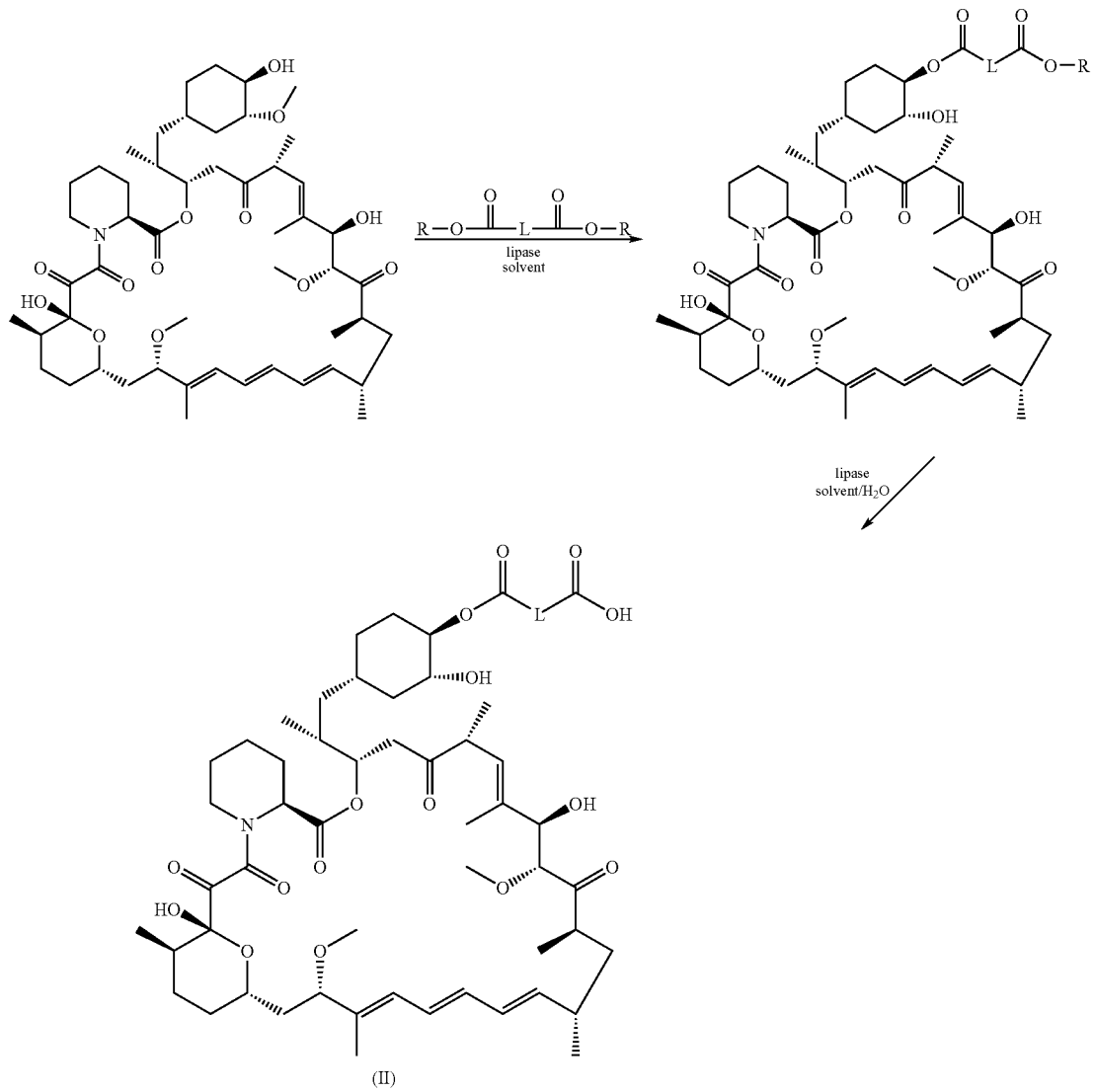

(II)

With reference to the bifunctional dicarboxylic ester,

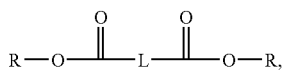

R is any suitable group that will activate the acyl group. One of skill in the art will readily recognize that a wide range of R groups can be utilized including, e.g., vinyl, isopropenyl, N-succinimidyl, 2,2,2-trifluoroethyl, 2,2,2-trichloroethyl, and oxime esters, among other. The selection of the activating group is not a limitation on the present invention. L is a linking group, as defined above. Examples of suitable L groups include those identified above, as well as a chain including one or more oxygen atoms, or alkylenes such as dimethylene ($CH_2CH_2$), trimethylene ($CH_2CH_2CH_2$), $CH_2OCH_2$, tetramethylene ($CH_2CH_2CH_2CH_2$), 2-methyltrimethylene [$CH_2CH(CH_3)CH_2$], pentamethylene ($CH_2CH_2CH_2CH_2CH_2$), hexamethylene ($CH_2CH_2CH_2CH_2CH_2CH_2$). These reagents are commercially available or can be prepared by methods described in the literature.

Similarly, an FK-506 32-hemiester can be prepared from an FK-506 and a bifunctional dicarboxylic ester using identical methods. It will be readily understood that where the following specification refers to rapamycin, FK-506 can be substituted, in order to produce an FK-506 32-hemiester.

In the first step, the reaction is performed as described in part I, with the exception that a bifunctional dicarboxylic ester is utilized in the place of a carboxylic anhydride. With these exceptions, the lipases and reaction conditions are as described in part I above.

One may select a solvent from among those identified in part I above. In one embodiment, the solvent can be selected from among those defined above, or from toluene, tert-butyl methyl ether (TBME), ethyl ether, isopropyl ether, hexane or mixtures thereof. In another embodiment, TBME is used. In one embodiment, TBME is used in an amount of at least 4 wt volume (i.e., a volume that is in an excess of 4 times (4×) the amount of rapamycin) to about 15 wt volume, or about 5 to 10 wt volumes.

Residual water can decompose rapamycin into a so-called, seco-rapamycin derivative, to form a macro lactone-ring opened product. In order to minimize this side-reaction, a low amount of moisture is maintained in the reaction system. In one embodiment, an anhydrous solvent is used with a standard commercial preparation of the lipase catalyst. In another embodiment, moisture can be controlled through adjusting the amount of water present in the lipase solution by adding a drying agent, such as $MgSO_4$, $Na_2SO_4$, among others. In still another embodiment, molecular sieves can be used to control the moisture. Many kinds of sieves with different pore size, including, 5 Å, 4 Å and 3 Å, among others, can be readily utilized. Suitable molecular sieves are available from a variety of commercial sources.

The enzymatic process of the invention can take place at a temperature in the range of about 20° C. to about 50° C., or about 25° C. to about 45° C. In one embodiment, the reaction is performed under $N_2$ to minimize the decomposition of rapamycin for 12 hours to 48 hours. The reaction can be monitored by various techniques such as thin layer chromatography (TLC) and high performance liquid chromatography (HPLC). Following reaction completion, the enzyme (lipase) is filtered off and the crude ester product is precipitated out by adding hexane, or heptane, to the filtrate.

The resulting ester intermediate is then subjected to lipase-catalyzed hydrolysis to recover the desired rapamycin 42-hemiadipate. The second step comprises the hydrolysis of crude ester intermediate from the first step in a wet solvent in the presence of a lipase. The lipase may be the same as the one used in the first step, or may be independently chosen from among the suitable lipases identified herein. In one embodiment, the lipase is lipase PS-C "Amano" II from Amano Enzyme, which is immobilized on ceramic particles chemically modified with a methylacryl group.

The medium used for this hydrolysis step may be chosen from among the solvents defined above or from water-immiscible solvents. In the case of a water-immiscible solvent, the solvent is saturated with water. More preferably, a water-miscible solvent is selected, including, e.g., MeCN, THF, dioxane, tert-amyl alcohol, acetone or mixture thereof, and a suitable amount of water, e.g., 0.5% v/v to 10% water v/v, or 1% v/v to 5% v/v.

In one embodiment, the temperature for this reaction is in the range of about 20° C. to about 50° C., or about room temperature (e.g., about 25° C.) to 35° C. In another embodiment, MeCN containing about 2% water is used as reaction medium, with about 20 wt % NOVOZYM SP 435 lipase at room temperature; the reaction is completed within a few hours.

In one embodiment, the hydrolysis step of this method of invention is conducted in accordance with the following procedure. Crude product from the first step is dissolved in a wet solvent. A sufficient amount of lipase is added and the mixture is then stirred at room temperature to 40° C. under argon (Ar) or nitrogen ($N_2$) atmosphere for 1 hour to 24 hours, or until all starting material is converted to the hemiester product of formula (II). This can be checked by conventional methods including, e.g., thin layer chromatography (TLC) or high performance liquid chromatography (HPLC). The enzyme is separated from the reaction mixture, e.g., via filtration. The crude product is then purified in excellent yield using conventional methods, e.g., silica gel chromatography or recrystallization.

In another embodiment, this two-step process can be performed in a one-pot fashion, i.e., the second hydrolysis step is carried out without the isolation of intermediate from the first step. In this one-pot process, the first enzymatic step is conducted as described above. Following completion of the reaction, a solvent and water are added. In one embodiment, the solvent is a water-miscible solvent, such as MeCN, THF, dioxane, tert-amyl alcohol, acetone or a mixture thereof. In yet another embodiment, the amount of water is from 0.5% v/v to 10% v/v, or 1% v/v to 5% v/v.

The mixture is then stirred for a certain period of time, the enzyme is filtered off, and the crude product is then purified by silica gel chromatography. In one embodiment, MeCN containing 5% water is added to the reaction mixture, and the reaction is completed within one hour.

This two-step enzymatic process for rapamycin 42-hemiester of formula (II) is further illustrated through the synthesis of rapamycin 42-hemiadipate via a two-step procedure (method 1) or a one-pot procedure (method 2) as shown in Example 2. The synthesis of 42-hemisuberate is shown in Example 3.

III. Compositions and Uses

Rapamycin 42-hemiesters and FK-506 32-esters with dicarboxylic acids produced according to the invention are useful precursors in preparing an immunogen, detector, and/or matrix-bound conjugate. These immunogens, detectors and conjugates are useful for the generation and detection of antibodies specific for the starting material (e.g., a rapamycin or a FK-506) or a derivative thereof, for measuring levels of the starting material or a derivative thereof, in biological or laboratory fluids, and for isolating binding proteins to the starting material or a derivative thereof.

As precursors for preparing rapamycin conjugates, the carboxylic acid in compounds of formula (II), prepared according to this invention, is activated using standard methodology described in the peptide literature. Typically this involves reacting the compound of the invention with N-hydroxysuccinimide to form an activated N-succinimidyl ester. This activated ester can then be reacted with the nucleophilic end of an immunogenic carrier molecule to form a rapamycin conjugate.

The following scheme exemplifies this technique.

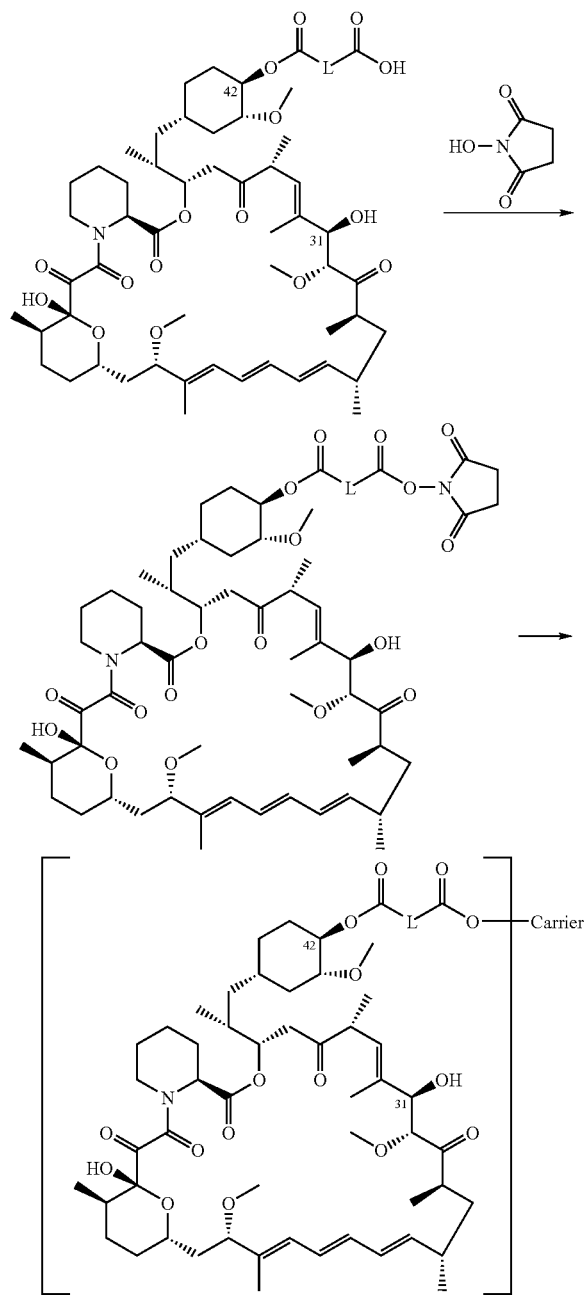

However, the invention is not so limited. Use of these and other rapamycin derivatives produced using the compounds of the invention is contemplated.

Antibodies specific for rapamycin or a derivative thereof using the rapamycin immunogen conjugates of this invention may be generated by standard techniques that are known in the art. In one embodiment, a host animal is inoculated at one or more sites with a purified regiospecific rapamycin 42-ester of the invention, either alone or in combination with an adjuvant. The antibodies generated from the rapamycin immunogen conjugates of this invention can be used in numerous immunoassays, for determining rapamycin levels, in ELISAs, radioimmunoassays, in chemiluminesence immunoassays, and in fluorescent immunoassays.

In another embodiment, the rapamycin 42-derivatives of the invention, or the conjugates or antibodies generated through the use thereof, can be formulated by any suitable method described in the art.

Similarly, methods for generating FK-506 immunogens, antibodies, and conjugates, from the KF-506 hemiesters of the invention will be readily apparent to one of skill in the art.

The present invention further provides packaging and kits containing the regiospecific rapamycin 42-hemiester produced according to the present invention and/or the FK-506 32-hemiester produced according to the invention, and formulated for their desired use, e.g., for antibody production. In another embodiment, the antibodies or rapamycin conjugates generated using the compositions of the invention can be formulated using a variety of suitable carriers, preservatives, or the like.

Suitable containers, including bottles, vials, blister packs, etc., are known to those of skill in the art. Such packaging and kits may contain other components, including, e.g., instructions for use, syringes, applicators, standard concentrations of rapamycin (for generation of a standard concentration curve), containers, microtiter plates, solid supports, test tubes, trays, etc. Many variations of reagents can be included in the kit depending on the type of assay used.

The following examples are intended to exemplify the present invention and should not be construed as limiting the claimed invention.

EXAMPLES

Example 1

Synthesis of Rapamycin 42-Hemisuccinate

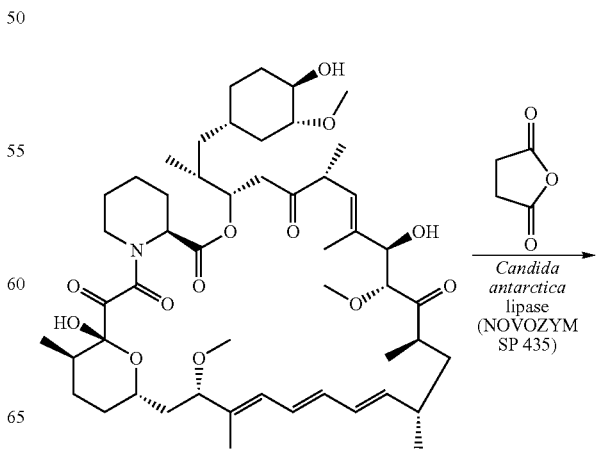

-continued

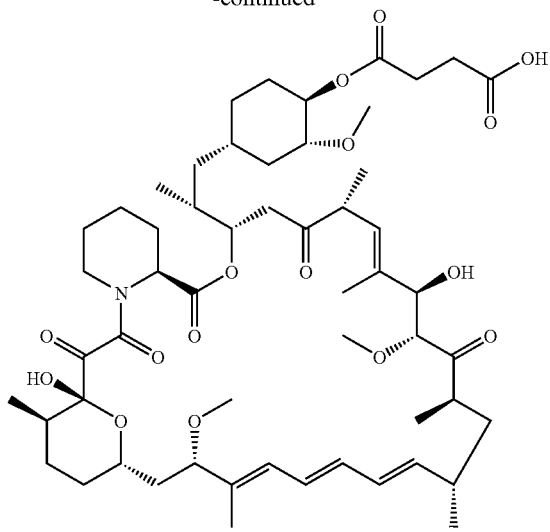

The lipase-catalyzed acylation is readily carried out by mixing rapamycin and succinic anhydride in a solvent with a lipase.

Method 1:

A mixture of rapamycin (2.0 g, 2.2 mmol), succinic anhydride (1.0 g, 10 mmol) and NOVOZYM SP435 (4.5 g) in toluene (20 mL) was stirred at 45° C. under $N_2$ atmosphere for 40 hours (40 h). The enzyme was filtered off and washed with toluene, the combined organic solvent was concentrated under reduced pressure. The residue was purified by silica gel column chromatography eluting with $CH_2Cl_2$-MeOH (12:1) to furnish the title compound as a white solid (2.02 g, 91% yield).

Method 2:

A mixture of rapamycin (91.4 mg, 0.1 mmol), succinic anhydride (120 mg, 1.2 mmol) and NOVOZYM SP435 (400 mg) in toluene-$CH_3CN$ (3 mL, 5:1 v/v) was stirred at 45° C. under $N_2$ atmosphere for 144 hours. The enzyme was filtered off and washed with toluene and the combined organic solvent was concentrated under reduced pressure. The residue was purified by silica gel column chromatography eluting with $CH_2Cl_2$-MeOH (12:1) to furnish the title compound as a white solid (87 mg), while rapamycin (10 mg) was recovered. The yield of 42-hemisuccinate is 96% based on the recovered rapamycin (86% based on the starting amount of rapamycin). MS: 1013 ($M^-$)

Example 2

Synthesis of Rapamycin 42-Hemiadipate

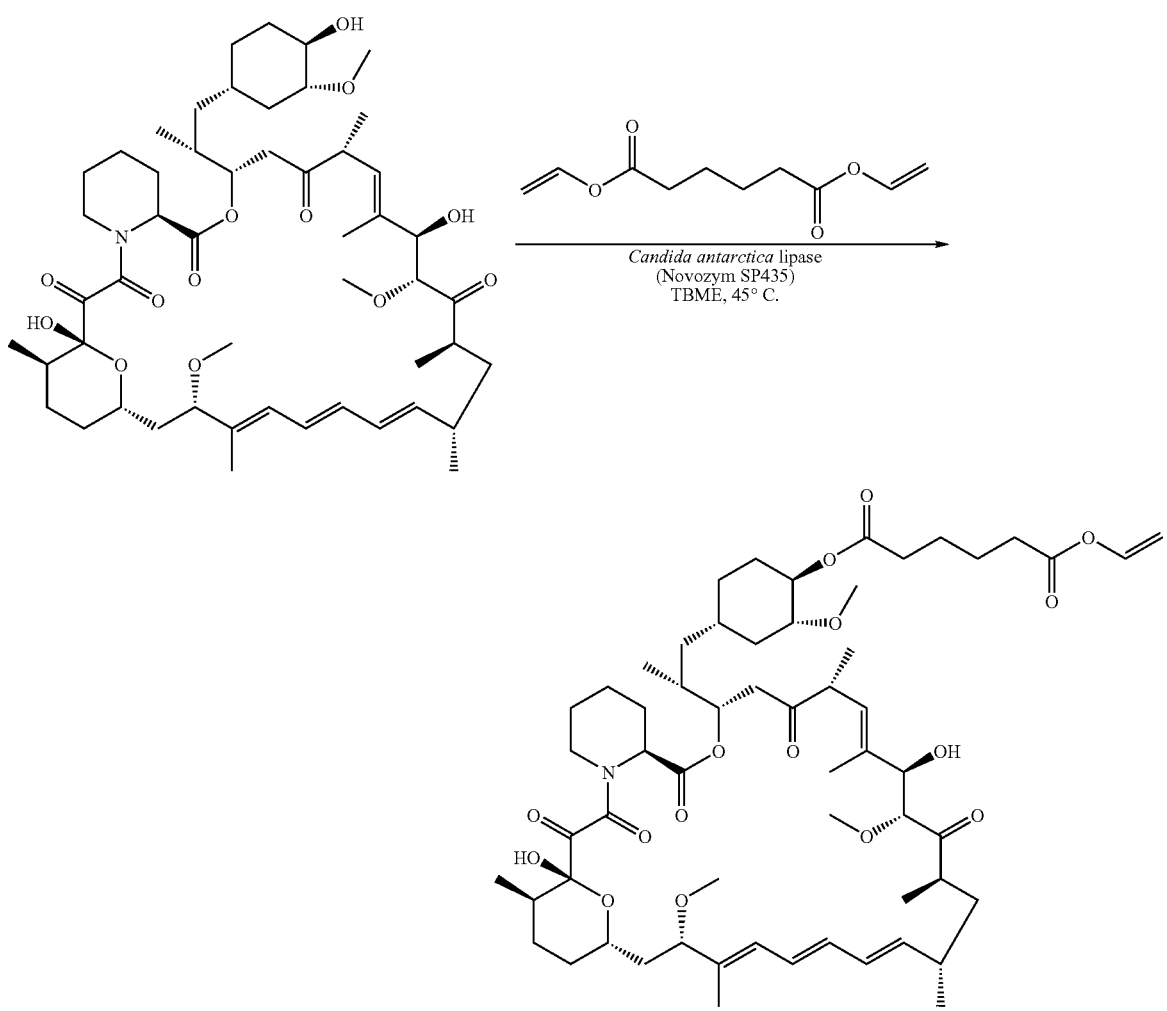

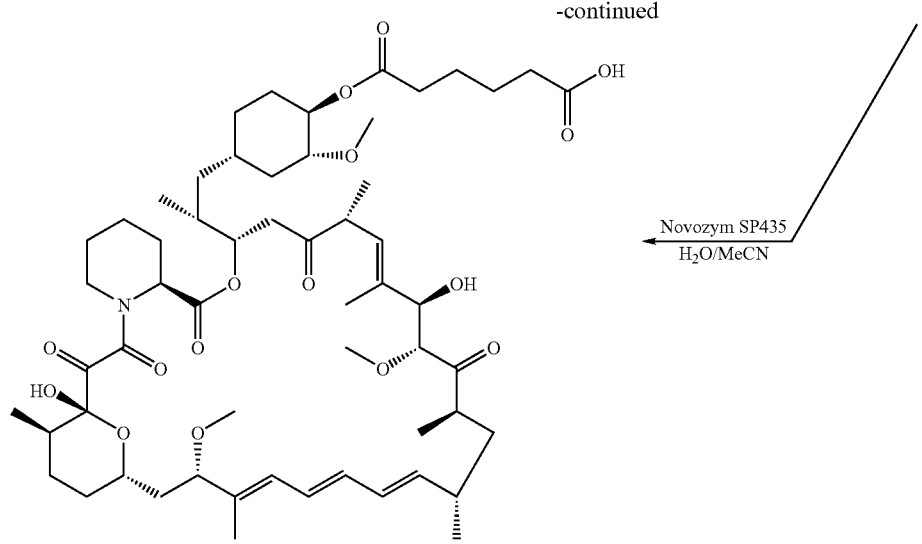

Method 1:

A mixture of rapamycin (457 mg, 0.5 mmol), divinyl adipate (250 mg, 1.25 mmol), 4 Å molecular sieves (80 mg) and NOVOZYM SP435 (300 mg) in t-butylmethyl ether (TBME) (4 mL) was stirred at 45° C. for 16 hours. The enzyme is removed by filtration and washed with 2×1 mL TBME. The filtrate is then added to ice-cold heptane (30 mL). The solid is collected on a Buchner funnel and the white powder is dried under vacuum for 2 hours.

The white powder is dissolved in 4 mL $CH_3CN$ [containing 2% (v/v) water]. NOVOZYM SP435 (80 mg) is added and the mixture stirred at room temperature for 1-2 hours. The enzyme is removed via filtration and washed with 2×1 mL MeCN. The filtrate is concentrated and residue is purified by silica gel flash chromatography eluting with $CH_2Cl_2$:MeOH (15:1) to furnish the title compound as a white solid (470 mg, 90% yield over two steps). MS: 1041 ($M^-$).

Method 2:

A mixture of rapamycin (3.0 g, 3.28 mmol), divinyl adipate (2.0 g, 10 mmol) and NOVOZYM SP435 (3.0 g) in anhydrous t-butylmethyl ether (TBME) (18 mL) was stirred at 40° C. for 36 hours. MeCN (10 mL, containing 5% $H_2O$) was added. After 15 minutes (15 min.), the enzyme is removed by filtration and washed with TBME/MeCN (2:1). Concentration and purification by silica gel flash chromatography eluting with hexane-acetone (5:4) afford title compound as a white solid (3.05 g, 89% yield).

Example 3

Synthesis of Rapamycin 42-Suberate

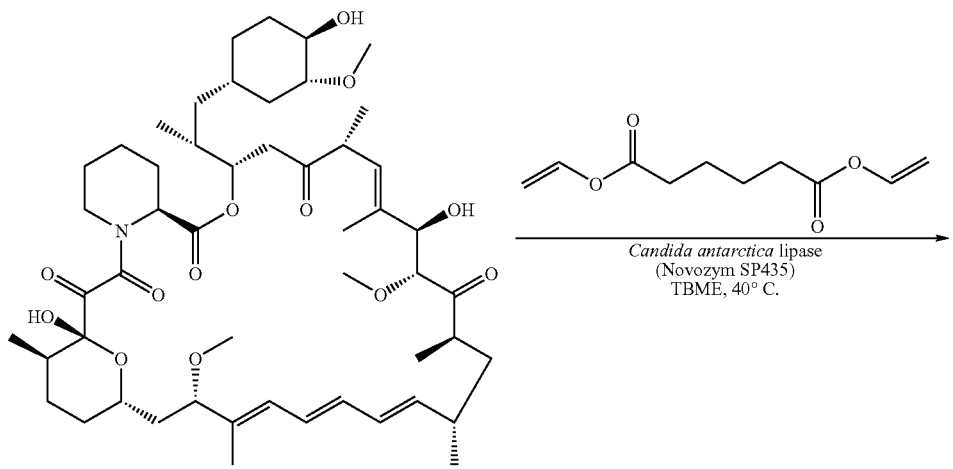

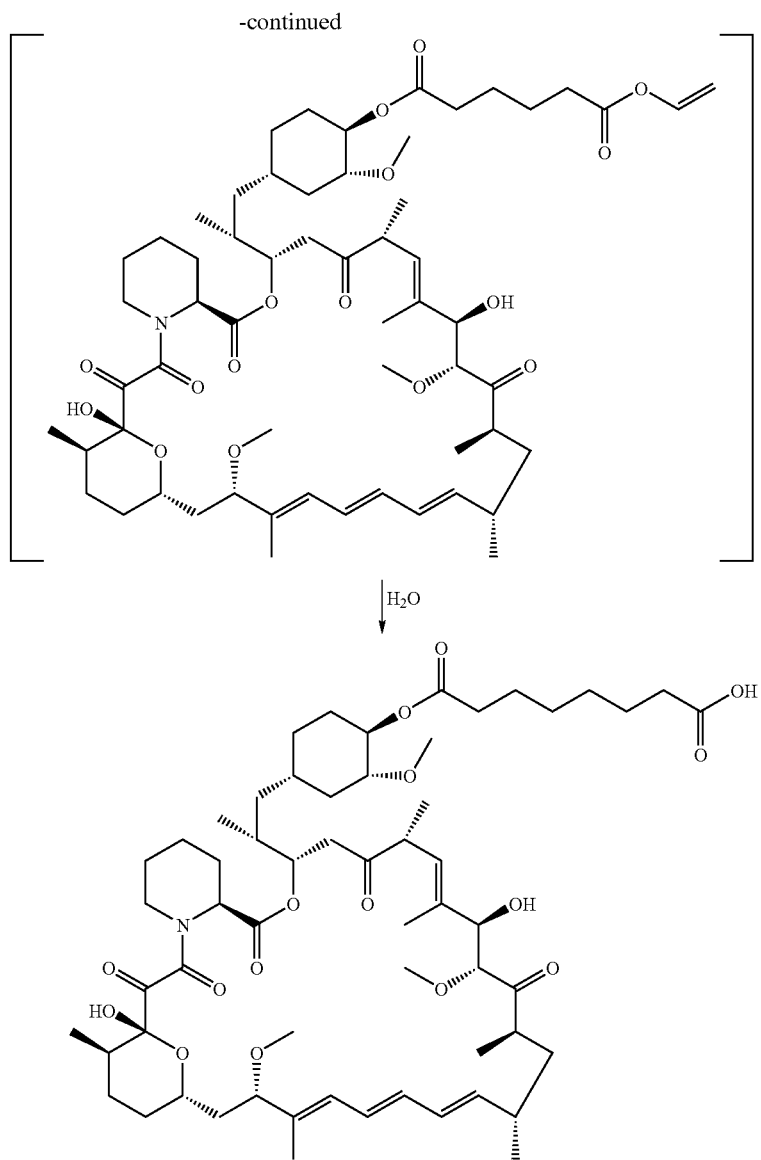

A mixture of rapamycin (3.0 g, 3.28 mmol), divinyl suberate (2.26 g, 10 mmol) and NOVOZYM SP435 (3.0 g) in anhydrous t-butylmethyl ether (TBME) (18 mL) was stirred at 40° C. for 48 hours. MeCN (10 mL, containing 5% $H_2O$) was added. After 15 min., the enzyme is removed by filtration and washed with TBME/MeCN (2:1). Concentration and purification by silica gel flash chromatography eluting with hexane-acetone (5:4) afford title compound as a white foam (2.88 g, 82% yield).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are listed throughout this application, the disclosures of which are incorporated herein by reference in their entireties. To the extent that a conflict may exist between the specification and a reference, the language of the disclosure made herein controls.

What is claimed is:

1. A method for the regiospecific synthesis of a rapamycin 42-hemiester or a FK-506 32-hemiester, said method comprising reacting a rapamycin or a FK-506 with a dicarboxylic anhydride in the presence of a lipase.

2. The method according to claim 1 for the regiospecific synthesis of a rapamycin 42-hemiester, said method comprising reacting rapamycin with said dicarboxylic anhydride in the presence of a lipase.

3. The method according to claim 1 for the regiospecific synthesis of a FK-506 32-hemiester, said method comprising reacting a FK-506 with said dicarboxylic anhydride in the presence of a lipase.

4. The method according to claim 1, wherein said dicarboxylic anhydride has the structure:

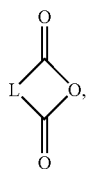

wherein L is a linking group with a straight chain or a branch chain having 1 to 6 carbon atoms.

5. The method according to claim 1, wherein said dicarboxylic anhydride is selected from the group consisting of succinic anhydride, glutaric anhydride, 3-methylglutaric anhydride, and mixtures thereof.

6. The method according to claim 1, wherein the lipase is a lipase from a microorganism selected from the group consisting of *Candida antarctica, Candida rugosa, Mucor miehei, Pseudomonas cepacia, Pseudomonas fluorescens, Rhizopus delemar*, and *Aspergillus niger*.

7. The method according to claim 6, wherein the lipase used is an immobilized lipase from *Candida antarctica*.

8. The method according to claim 1, wherein the reaction is conducted in a solvent selected from the group consisting of toluene, tert-butyl methyl ether (TBME), tetrahydrofuran (THF), acetonitrile (MeCN), 1,4-dioxane, $CH_2CH_2$, $CHCl_3$, ethyl ether, hexane, and mixtures thereof.

9. The method according to claim 1, wherein the reaction is conducted in the range of 20° C. to 75° C.

10. The method according to claim 9, wherein the reaction is conducted in the range of 35° C. to 60° C.

11. The method according to claim 1, wherein said lipase is NOVOZYM SP435 lipase, the solvent is a mixture of toluene-acetonitrile at a ratio of 5:1 v/v, and the reaction is conducted at a temperature of about 45° C.

12. A method for the regiospecific synthesis of a FK-506 32-hemiester, said method comprising:
(a) reacting a FK-506 with a bifunctional activated ester of a dicarboxylic acid in the presence of a lipase to form an ester intermediate, and
(b) hydrolyzing the ester intermediate with a lipase.

13. The method according to claim 12, wherein the bifunctional ester of the dicarboxylic acid has the structure:

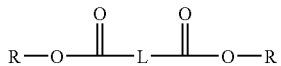

wherein:
R is vinyl, isopropenyl, or N-succinimidyl; and
L is a linking group with a straight chain or a branch chain having 1 to 6 carbon atoms.

14. The method according to claim 13, wherein L further comprises one or more oxygen atoms.

15. The method according to claim 12, wherein the lipase used in step (a) is selected from a lipase from a microorganism selected from the group consisting of *Candida antarctica, Candida rugosa, Mucor miehei, Pseudomonas cepacia, Pseudomonas fluorescens Rhizopus delemar*, and *Aspergillus niger*.

16. The method according to claim 15, wherein the lipase used in the step (a) is NOVOZYM SP435 from *Candida antarctica* or Lipase PS-C "Amano"II from *Pseudomonas cepacia*.

17. The method according to claim 12, wherein the reaction of step (a) is conducted in a solvent selected from the group consisting of toluene, tert-butyl methyl ether (TBME), tetrahydrofuran(THF), MeCN, 1,4-dioxane, $CH_2Cl_2$, $CHCl_3$, ethyl ether, hexane, and a mixture thereof 18. The method according to claim 17, further comprising adding molecular sieves to the reaction.

19. The method according to claim 12, wherein the reaction of step (a) is conducted in the range of 20° C. to 75° C.

20. The method according to claim 12, wherein the lipase used in step (a) is selected from NOVOZYM SP435 or lipase PS-C "Amano" II, the solvent is TBME, and the reaction is conducted at a temperature of about 45° C.

21. The method according to claim 12, wherein the lipase used in the step (b) is a lipase from a microorganism selected from the group consisting of *Candida antarctica, Candida rugosa, Mucor miehei, Pseudomonas cepacia, Pseudomonas fluorescens, Rhizopus delemar*, and *Aspergillus niger*.

22. The method according to claim 21, wherein the lipase used in step (b) is from *Candida antarctica* or *Pseudomonas cepacia*.

23. The method according to claim 12, wherein the hydrolysis of step (b) is performed in a solvent selected from the group consisting of toluene, tert-butyl methyl ether (TBME), tetrahydrofuran (THF), MeCN, 1,4-dioxane, tert-amyl alcohol, $CH_2Cl_2$, $CHCl_3$, ethyl ether, hexane, and mixture thereof, said solvent or solvent mixture containing about 0.5 to 10% water.

24. The method according to claim 12, wherein the hydrolysis of step (b) is conducted in the range of room temperature to 50° C.

25. The method according to claim 12, wherein the lipase used in step (b) is NOVOZYM SP435 or lipase PS-C "Amano" II, the solvent is acetonitrile (MeCN) containing 2% water, and the reaction is conducted at room temperature.

* * * * *